US007252996B2

(12) United States Patent
Boccaccio et al.

(10) Patent No.: US 7,252,996 B2
(45) Date of Patent: Aug. 7, 2007

(54) ANCILLARY COMPOSITION FOR THE PREPARATION OF COMMITTED MATURE DENTRITIC CELLS

(75) Inventors: Claire Boccaccio, Paris (FR); Alessandra Nardin, Paris (FR); Jean-Pierre Abastado, Paris (FR)

(73) Assignee: I.D.M. Immuno-Designed Molecules, Paris (FR)

( * ) Notice: Subject to any disclaimer, the term of this patent is extended or adjusted under 35 U.S.C. 154(b) by 68 days.

(21) Appl. No.: 10/466,186

(22) PCT Filed: Dec. 29, 2001

(86) PCT No.: PCT/EP01/15314

§ 371 (c)(1),
(2), (4) Date: Dec. 19, 2003

(87) PCT Pub. No.: WO02/055675

PCT Pub. Date: Jul. 18, 2002

(65) Prior Publication Data

US 2004/0197901 A1  Oct. 7, 2004

(30) Foreign Application Priority Data

Jan. 15, 2001  (EP)  .................................. 01400109

(51) Int. Cl.
*C12N 5/02* (2006.01)
(52) U.S. Cl. ...................... 435/377; 435/355; 435/372
(58) Field of Classification Search ................ 435/375; 424/93.1
See application file for complete search history.

(56) References Cited

U.S. PATENT DOCUMENTS

2001/0026937 A1* 10/2001 Punnonen et al. .......... 435/366

FOREIGN PATENT DOCUMENTS

WO   WO 99 47646      9/1999
WO   WO 02/074939 A1  9/2002

OTHER PUBLICATIONS

Chakraborty et al. Stimulatory and inhibitory differentiation of human myeloid dendritic cells. Clinical Immunology (Feb. 2000), vol. 94, No. 2, pp. 88-98.*
Pascale Jeannin et al., "OmpA Targets Dendritic Cells, Induces Their Maturation and Delivers Antigen into the MHC Class I Presentation Pathway," Nature Immunology, V. 1, 2000, pp. 502-509.
Haeuw, Jean-Francois et al., "The recombinant *Klebsiella pneumoniae* outer membrane protein OmpA has carrier properties for conjugated antigenic peptides", Eur. J. Biochem. 255, 1998, pp. 446-454.
Nguyen, Thien Ngoc et al., "Chromosomal sequencing using a PCR-based biotin-capture method allowed isolation of the complete gene for the outer membrane protein A of *Klebsiella pneumoniae*", Gene 210, 1998, pp. 93-101.
Jongmans, Wim et al., "Th1-Polarizing Capacity of Clinical-Grade Dendritic Cells is Triggered by Ribomunyl but Is Compromised by $PGE_2$ ", J Immunother, vol. 28, No. 5, Sep./Oct. 2005, pp. 480-487.
Peng, Judy C. et al., "Generation and Maturation of Dendritic Cells for Clinical Application Under Serum-Free Conditions", J Immunother, vol. 28, No. 6, Nov./Dec. 2005, pp. 599-609.
Barrou, Benoit et al., "Vaccination of prostatectomized prostate cancer patients in biochemical relapse, with autologous dendritic cells pulsed with recombinant human PSA", Cancer Immunol. Immunother., 53, 2004, pp. 453-460.
Boyer, Aurelie et al., "Generation of phagocytic MAK and MAC-DC for therapeutic use: Characterization and in vitro functional properties", Experimental Hematology, 27, 1999, pp. 751-761.
Letters to the Editor, Adoptive Immunotherapy of Ovarian Carcinoma, Gynecologic Oncology, 86, 2002, pp. 102-103.
Salcedo, M. et al., "Vaccination of melanoma patients using dendritic cells loaded with an allogeneic tumor cell lysate", Cancer Immunol. Immunother. , 2005.
Thiounn, Nicolas et al., "Adoptive Immunotherapy for Superficial Bladder Cancer with Autologous Macrophage Activated Killer Cells", The Journal of Urology, vol. 168, Dec. 2002, pp. 2373-2376.
Salcedo, M. et al., "Preclinical and clinical development of a DC-based melanoma therapeutic vaccine", Sep. 5-7, 2005, Lisbon, Portugal.
"Characterization of a functional property of MD-APCs according to the invention: Antibody Dependent Cell Cytotoxicity (ADCC) assay", APC USA 09/194,053, priority EP 96 401 099.5, May 21, 1996.
Coronel, Agnes et al., "Cytokine production and T-cell activation by macrophage-dendritic cells generated for therapeutic use", British Journal of Haematology, 2001, 114, pp. 671-680.
Tsuji et al:, "Maturation of Human Dendritic Cells by Cell Wall Skeleton of Mycobacterium Bovis Bacillus Calmette-Guerin: Involvement of Toll-Like Receptors", Infection and Immunity, vol. 68, No. 12, - Dec. 2000, pp. 6883-6890, XP000995248, *See abstract Materials and Methods, esp. p. 6884, RH column third paragraph, Results, Discussion* the whole document.
Banchereau and Steinman: "Dentritic Cells and the Control of Immunity" Nature, vol. 392, Mar. 19, 1992, pp. 245-252, XP002134557 *see whole document, especially *p. 246, column 2, paragraph 2.
Revillard et al:., "In Vitro Cell Activating Properties of the Composite Ribosomal Vaccine D53" Mem. Inst. Oswaldo Cruz, vol. 82, No. Suppl. II, 1987, pp. 173-178, XP000995084, Rio de Janeiro * see whole document, especially * p. 177, column 2, paragraph 1.
Caux et al.: "Gamma-Interferon Enhances Factor-Dependent Myeloid Proliferation of Human CD34+ Hematopoietic Progenitor Cells" Blood, vol. 79, No. 10, May 15, 1992, pp. 2628-2635, XP002043207, * see entire document , especially * p. 2629, column 2, paragraph 2 -p. 2630, column 2, paragraph 1.

* cited by examiner

*Primary Examiner*—James Ketter
(74) *Attorney, Agent, or Firm*—Young & Thompson

(57) ABSTRACT

The invention consists in the use of a maturation agent comprising a mixture of ribosomal and/or membrane fractions for the preparation of mature dendritic cells from immature dendritic cells.

20 Claims, 6 Drawing Sheets

ANCILLARY COMPOSITION FOR THE PREPARATION OF COMMITTED MATURE DENTRITIC CELLS

The present invention relates to a method for the production of committed mature dendritic cells (DCs) and particularly to a cocktail of ribosomal and/or membrane bacterial extracts used for the DCs maturation.

Dendritic cells are defined as the most potent antigen presenting cells able to stimulate both primary and secondary immune responses against specific exogenous antigen (Hart "Dendritic cells: unique leucocyte populations which control the primary immune response" Blood, 1997, vol. 90, p3245). In vivo, immature dendritic cells that have captured antigens in the periphery migrate through lymphatic vessels to T cell zones of lymphoid organs where they present epitopes deriving from these antigens in the context of MHC molecules and allow activation and proliferation of antigen-specific naive T cells.

Stimulated lymphocytes can be cytotoxic or auxiliary, but also regulatory or suppressive lymphocytes, depending on the type of the dendritic cells and on the pre-existing cytokine pattern.

During migration, dendritic cells undergo a maturation process that results in morphological and phenotypical changes. Maturation induces a reduced capacity of DCs to capture antigens and an increased capacity of antigen presentation. Maturing DCs express higher levels of costimulatory molecules, acquire the expression of CD83 on their surface, they produce cytokines stimulating effector T cell subtypes and acquire migratory abilities (for a review, see "Immunobiology of dendritic cells", Banchereau et al., 2000, Ann. Rev. Immunol., 18:767-811).

Possibilities for preparing ex vivo large quantities of dendritic cells have recently been developed, followed by a growing interest for the use of these cells in immunotherapy and as cellular vaccines.

Dendritic cells can be obtained from different tissue sources or form precursors present in blood or in bone marrow. Immature dendritic cells may be obtained from blood cells by differentiating monocytes using defined culture conditions (Boyer et al., "Generation of phagocytic MAK and MAC-DC for therapeutic use: Characterization and in vitro functional properties", Exp. Hematol. 1999, vol.27, pp751-761). Proliferating dendritic cells progenitors have also been identified within the small CD34+ subfraction of cells in human blood (Inaba et al. "Identification of proliferating dendritic cells precursors in mouse blood", 1992, J. Exp. Med., vol.175, p1157) and methods have been developed to differentiate these cells.

After being differentiated from blood monocytes, for example in presence of IL-13, dendritic cells present an immature phenotype: they are powerful for the antigen capture by pinocytosis or phagocytosis, exhibit low levels of the costimulation molecule CD80 and do not express the surface marker CD83 Moyer et al, 1999).

Mature dendritic cells are more potent immune modulators than immature DCs. In particular, the capacity of dendritic cells to induce an immune response in vivo has been correlated to their degree of maturation (Labeur M. S et al "Generation of tumour immunity by bone-marrow derived dendritic cells correlates with dendritic cell maturation stage", J. Immunol., 1999,162, 168-175).

There are several known agents used for the maturation of DCs for research purposes, such as poly IC, ligands of CD40, anti-CD40 antibodies, endotoxins, living bacterias, culture supernatants and cocktail of agonistic cytokines, including TNFα. However, clinical trials for which patients are vaccinated with mature dendritic cells are under development, using cells presenting foreign antigens on their surface after being pulsed with peptides or loaded with particulate antigens. It is therefore required to develop reproducible clinical grade maturation conditions to obtain of committed mature dendritic cells with defined immunomodulatory capacity.

*Mycobacterium bovis bacillus* Calmette-Guérin (BCG) is shown to activate dendritic cells (Kim et al., "Enhanced antigen-presenting activity and tumour necrosis factor a-independent activation of dendritic cells following treatment with *Mycobacterium bovis bacillus* Calmette-Guérin", Immunology, 1999, vol.97, pp 626-633). However, BCG is a living attenuated bacterial strain, and its use in a cellular vaccine presents several drawbacks including safety concerns.

Ribomunyl® (International Non-proprietory Name, or Generic name: Ribosomal and membranar bacterial fractions, membranar proteoglycanes) is known for its non specific natural immunostimulatory effect. It contains both proteoglycans from *Klebsiella pneumoniae* (0.015 mg in a dose of lyophylisate) and ribosomal fractions containing 70% RNA from 4 different bacterial strains, *Klebsiella pneumoniae* (35 parts), *Streptococcus pneumoniae* (30 parts), *Streptococcus* pyogenes group A (30 parts) and *Haemophilus influenzae* (5 parts) (0.01 mg of ribosomal extracts in a dose of lyophylisate). The proteoglycans act as an adjuvant and a nonspecific immunostimulant, whereas the immunogenicity of the ribosomes is attributed either to peptides naturally bound to ribosomes or to epitopes bound to membrane and cytoplasmic ribosomes (Clot et al "Pharmacology of ribosomal immunotherapy", Drugs, 1997, vol.54, suppl.1, pp 33-36). Ribomunyl®, also designed as RBL, triggers mucosal immune responses (Béné & Faure, "From Peyer's patches to tonsils", Drugs, 1997, 54, suppl.1, pp24-28). RBL was shown to stimulate the general innate immune response by acting on polymorphonuclear cells (PMNs) and macrophages, to increase the production of several cytokines (IL-1, IL-6, IL-8, TNFα, CSF), and to be able to activate natural killer cells.

The aim of the present invention is to provide a new process for the preparation of mature dendritic cells from immature dendritic cells. This process comprising the step of contacting, in a culture medium, immature dendritic cells with a maturation agent comprising a bacterial mixture of ribosomal and/or membrane fractions.

The term "maturation" is defined as the action on immature highly phagocytic dendritic cells, resulting into phenotypic and/or functional modification of the cells. The associated phenotypic modifications are the increase in CD86, CD86, CD83, MHC class I and II molecules cell surface expression and the decrease in CD14 surface expression. The functional changes may be the loss of phagocytic properties, the acquisition of migration abilities, an increased allogeneic T cells stimulation efficiency and changes in the cytokine and chemokine expression profile, and particularly an increased IL-12 secretion. The IL-12 production by DCs is critical for their in video function, since this cytokine has been shown to generate a polarization of the immune response towards the Th1 pathway in vivo. A Th1 type response is considered as immune response, involving stimulation of antigen specific T lymphocytes CD8+, whereas a Th2 type immune involves rather a stimulation of antibody response and eventually unresponsiveness of the cytotoxic lymphocytes to an antigen.

The term "committed DCs" is defined as mature DCs directing the immune response clearly towards Th1 immunostimulation or towards immunoregulation.

The term "ribosomal extracts" is defined as bacterial extracts containing ribosomal fractions, and particularly single and/or double stranded ribonucleic acid. Ribosomal extracts or fractions correspond to any extract containing ribosomes, purified or partially purified from a bacterial culture. The process of preparation of such extracts comprises at least a step of lysis of the bacteria obtained after the culture, and a step of separation of the fraction containing bacterial ribosomes from the total lysate, in particular by centrifugation or filtration.

The term "membrane extracts" is defined as bacterial extracts enriched in membrane fractions. Membrane extracts or fractions correspond to any extract or fraction containing membranes, purified or partially purified from a bacterial culture. The process of preparation of such extracts comprises at least a step of lysis of the bacteria obtained after the culture, and a step of separation of the fraction containing bacterial membranes, in particular by centrifugation or filtration.

The different bacterial fractions can be prepared according to methods known by a man skilled in the art, such as a method described by Haeuw J. F. et al (Eur. J. Biochem., 255, 446-454, 1998), or such as a method described in U.S. Pat. No. 4,249,540, filed by Pierre Fabre S. A.

The term "bacterial mixture" is defined as a mixture of bacterial extracts, possibly originating from different bacterial strains, comprising membrane and ribosomal fractions.

The term "maturation medium" is defined as a culture medium appropriate for the cells survival and differentiation, in which is added a maturation agent, such a culture medium being liable to be supplemented.

According to an embodiment of the invention, the process for the preparation of mature dendritic cells is characterized in that the maturation agent comprises a bacterial mixture of ribosomal and membrane fractions and interferon-γ (IFN-γ). The interferon-γ has a synergistic effect to the maturation agent to increase maturation characteristics of DCs and their stimulating phenotype. A "stimulating phenotype" of the dendritic cells is defined as inducing Th1 response and secreting a cytokine profile favouring cytotoxic T lymphocytes.

According to another embodiment of the invention, the process is characterized in that immature dendritic cells are contacted with a maturation agent comprising membrane fractions being from *Klebsiella pneumoniae*. Such maturation agents may be used at concentrations from about 0.01 to about 100 μg/ml, and preferably of about 0.1 to about 10 μg/ml in the maturation medium.

According to another embodiment of the invention, the process is characterized in that immature dendritic cells are contacted with a maturation agent comprising ribosomal fraction being from the bacterial strains *Klebsiella pneumoniae, Streptococcus pneumoniae, Streptococcus* pyogenes group A and *Haemophilus influenzae*. Such maturation agents may be used at concentrations from about 0.01 to about 100 μg/ml, and preferably of about 0.1 to about 10 μg/ml in the maturation medium.

In a particular embodiment of the invention, immature dendritic cells are contacted with a maturation agent comprising a bacterial mixture of ribosomal and membrane extracts used at a dose of about 0.01 to about 100 μg/ml, and preferably of about 0.1 to about 10 μg/ml in the maturation medium.

In a particular embodiment of the invention, the maturation agent is Ribomunyl® (Inava Laboratory, Pierre Fabre).

In another particular embodiment of the invention, immature dendritic cells are contacted with a maturation agent comprising a bacterial cocktail of ribosomal and membrane extracts and interferon-γ at a dose of 10 to 10000 UI/ml, and preferably from about 100 to about 1000 UI/ml. Ability of IFN-γ to increase the maturation effect was tested and found to be effective in particular on the dendritic cells IL-12 secretion (see example 3). When comparing the effects on the cytokine secretion of contacting immature dendritic cells with a maturation agent comprising Ribomunyl® (RBL) alone, or with a maturation agent comprising RBL and IFN-γ, or with a known maturation agent, such as poly I:C combined to anti-CD40, the contact of cells with RBL and IFN-γ leads to an IL-12 secretion level superior to that obtained with the other maturation agents, and the contact of cells with RBL induces an IL-10 secretion level superior to the other maturation agents (see example 3). The ratio between the level of IL-12 secretion and the level of IL-10 secretion shows that when both RBL and IFN-γ are used, the cells are effectively committed towards an immunostimulating mature dendritic cells phenotype.

On the other hand, the obtention of DCs having a higher IL10 secretion level and a lower IL12 secretion level, using for example RBL alone as a maturation agent, leads to mature dendritic cells possessing interesting immunoregulatory properties, in particular to control auto-immune diseases.

The present invention also relates to a process for the preparation of antigen loaded mature dendritic cells. Cells may be antigen loaded by phagocytosis, pinocytosis, affinity binding, fusion, nucleic acid (DNA, RNA) transfer or receptor mediated uptake, according to methods known by a man skilled in the art. The dendritic cells culture medium may be completed with soluble or particulate antigens, including tumour target cells or cell debris, or specific peptides against which an immune response is expected. The culture medium may also be supplemented with genetic material coding for a peptide or a protein against which a modulation of the immune response is desired, this genetic material being linked to a vector able to allow the transfection of the dendritic cells.

Where it is desirable for cells to take up antigens by phagocytosis, it is preferable to add antigen to the culture of immature dendritic cells prior to addition of the dendritic cells maturation factor. Phagocytosis may be desirable when particulate antigens, cell lysates or immune complexes are used. When soluble peptide antigens are used, it is preferable to expose the antigen to dendritic cells after a meanwhile maturation.

The present invention also concerns the dendritic cells liable to be obtained according to the process described in the present application.

Immature DCs might be obtained by any method known by a man skilled in the art. As an example monocyte derived dendritic cells can be prepared according to patent applications WO 94/26875, WO 96/22781 or WO 97/44441. Dendritic cells may also been prepared according to Bancereau et al ("Immunobiology of dendritic cells" Annu. Rev. Immunol., 2000, 18:767-911).

Dendritic cells liable to be obtained according to the process of the invention are able to act on precise T cells subpopulations. This means that the dendritic cells according to the invention are able to stimulate or to regulate Th2/Th1 immune response. DCs are able to induce in vivo antigen-specific proliferation of T cells, thus leading to antigen specific increased cytotoxicity and immunostimulation, or to induce in vivo regulatory T cells and therefore inhibition of antigen-specific cytotoxic T cells, leading to unresponsiveness to a specific antigen. The balance between immunostimulatory and immunoregulatory capacity of the mature dendritic cells depends on the maturation conditions applied to the immature cells and on the type of DCs submitted to these conditions.

A induced immune response might be characterized by an in vivo clinical immune response against a given pathogen or a tumour, leading to its decrease or its elimination. In vitro, this may be measured, for dendritic cells, in a immunostimulation assay of antigen-specific cytotoxic T lymphocytes. The functionality of dendritic cells treated according to the invention may be measured as their target recognition capacity and by an analysis of their cytokine and chemokine release. A regulated immune response might be observed clinically, in the case of an auto-immune disease, by the decrease or disappearance of the symptoms. In vitro, antigen presenting cells able to regulate an immune response are characterized by their reduced secretion of stimulatory cytokines (IL-1, IL-12, IFN-γ) and their increased secretion of certain inhibiting cytokines (IL 10, TGF-β).

The cell morphology of dendritic cells after treatment with Ribomunyl® and IFNγ is characterized by the presence of dendrites, whereas they are not visible on immature dendritic cells Banchereau et al., 2000).

The flow cytometry analysis of the phenotype of the cells after a 40 hours contact with a maturation agent comprising either RBL alone or RBL plus interferon-γ shows that the dendritic cells population is only partially maturated, as evidenced for example by the CD83 expression pattern (see FIG. 3). This partial maturation could possibly allow the dendritic cells to pursue their maturation process in vivo, after being injected to the patient. In particular, such cells could be able to efficiently migrate from their injection point to lymph nodes. This property may open interesting possibilities for in vivo therapeutic applications.

The examples cited in the present application indicate a contact between dendritic cells and the maturation agent during 40 hours. However the process according to the invention may comprise a step of contacting immature dendritic cells with a maturation agent during 18 hours or even during a shorter time, according to the expected maturation level of the dendritic cells.

Dendritic cells liable to be obtained according to the process are usable for immunotherapy and for vaccinology. Administration of the cells to a patient is possible, the cells and additives being of clinical grade.

The present invention also concerns pharmaceutical compositions containing as active substance dendritic cells liable to be obtained according to the process described in the application.

The present invention also concerns cellular vaccine composition containing as active substance dendritic cells liable to be obtained according to the process described in the application.

Pharmaceutical compositions, cellular vaccine compositions and immunotherapeutic drugs containing antigen presenting cells prepared according to the methods described might be administered to patients under various galenic forms comprising the intradermal, subcutaneous, intraveinous, intralymphatic, intranodal, intramucosal or intramuscular administration The number of dendritic cells in a single dose injected is comprised from about $10^6$ to about $10^9$ cells for a patient, and preferably from about $10^7$ to about $10^8$ cells for a patient for a single dose. As an example, the patient may receive one injection each week, during six successive weeks.

Immature DCs were incubated during 40 hours in the presence of doses ranging from 0.001 to 10 μg/ml of Ribomunyl. To follow maturation, DCs were stained with anti-CD83 antibodies, anti-CD86 and anti-HLA ABC antibodies and the fluorescence analysed with flow cytometer.

The X axis represents the doses used of Ribomunyl, in μg/ml within the maturation medium. The expression of the markers is expressed, for CD86 and HLA-ABC markers, as Mean Fluorescence Intensity arbitrary units (left Y axis) and for CD83 marker as percentage of cells expressing the markers (right Y axis). The clear and dark histograms corresponds respectively to the CD86 and to the HLA-ABC expression, whereas the curve represents the percentage of cells expressing CD83 marker.

Figure 2:
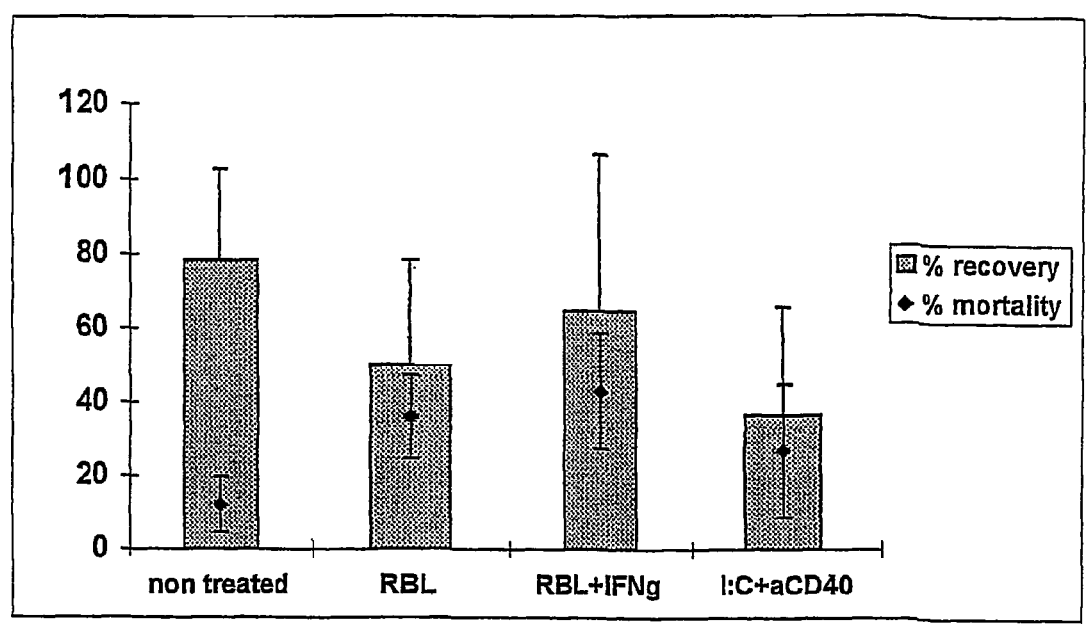

FIG. 2: DCs recovery and mortality upon different maturation conditions.

Immature DCs were incubated for 40 hours in the presence of standard reagents anti-CD40 (3 μg/ml) and poly(I:C) (100 μg/ml), in the presence of the clinical grade reagents Ribomunyl (1 μg/ml) or Ribomunyl (1 μg/ml) and IFN-γ at 1000 UI/ml. Cell recovery after culture was estimated by counting living cells under the microscope on Malassez slide. Cell viability was measured by FACS using TOPRO-3 technology (Molecular Probes)

The X axis represents the different maturation condition used, whereas the Y axis represents the percentage of cells recovered or the percentage of cells mortality. The histograms correspond to the expression of cells recovery, the lozenges correspond to the percentage of cell mortality.

Figure 3:
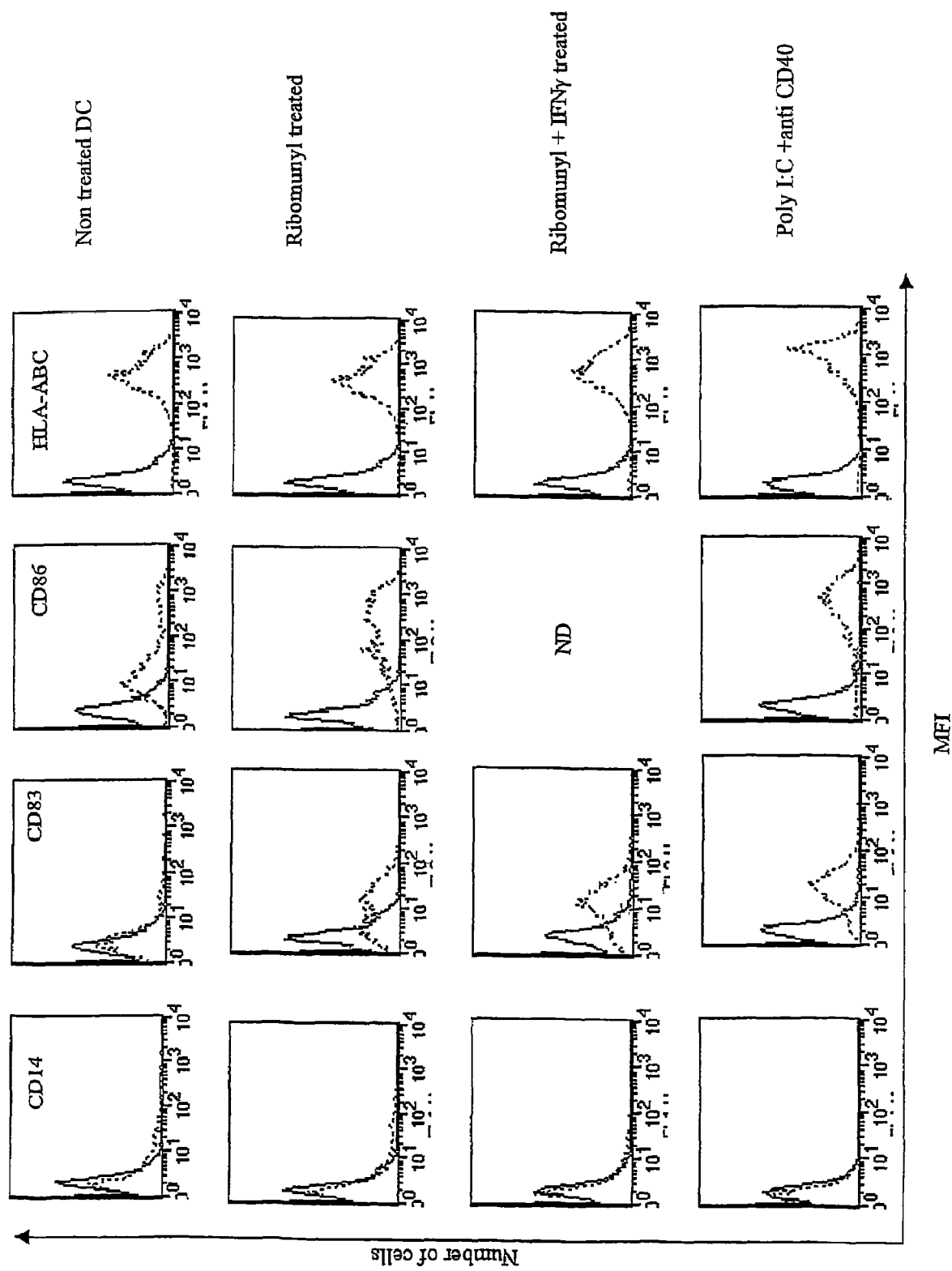

FIG. 3: Phenotypic FACS analysis of DCs without any maturation treatment and after incubation with different maturation agents.

Immature DCs were incubated for 40 hours in the presence of standard reagents anti-CD40 (3 μg/ml) and poly(I:C) (100 μg/ml), in the presence of the clinical grade reagent Ribomunyl (1 μg/ml) or Ribomunyl (1 μg/ml) and IFN-γ at 1000 UI/ml. The fulllines corresponds to an isotype control. The dotted lines correspond to the samples analysis.

Figure 4:
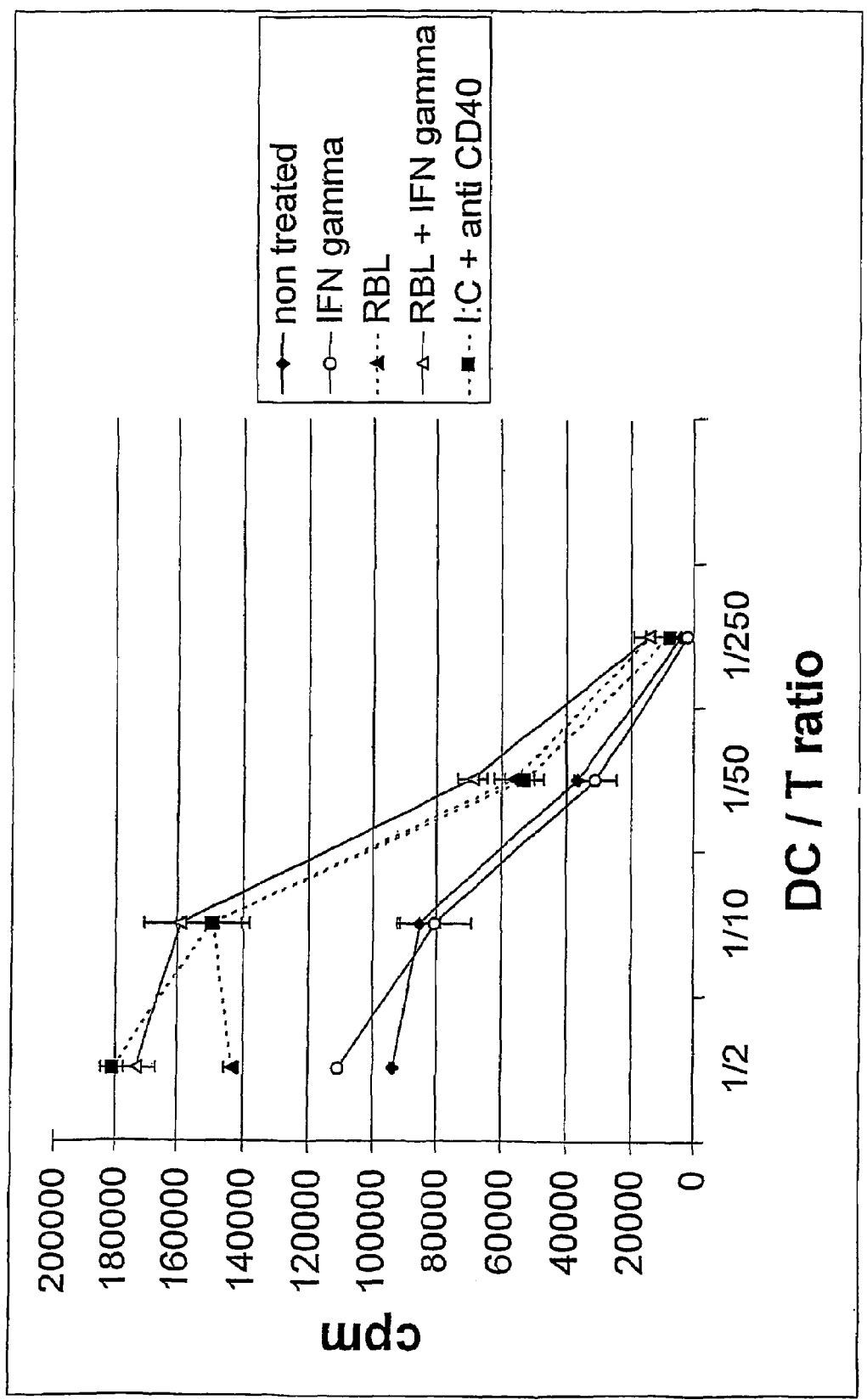

FIG. 4: T cells allogeneic stimulation of mature DCs

Allogeneic mixed lymphocyte reaction (MLR) was performed on DCs matured either by treatment with clinical grade RBL (1 μg/ml), RBL (1 μg/ml)+IFN-γ (1000 U/ml), poly I:C+anti-CD40 or with IFN-γ alone (1000 UI/ml) and on immature DCs. DCs were incubated during 5 days with a fixed number of allogeneic T lymphocytes present in a peripheral blood leukocyte extract. Cell proliferation was quantified by [$^3$H] thymidine uptake of cells incubated with 1 μCi of [methyl-3H] thymidine during the last 18 hours of culture.

The X axis represents the different DCs/T cells ratios, whereas the Y axis corresponds to the quantification of [$^3$H] thymidine uptake of the cells. Dark lozenges represent values obtained with non treated DCs (=immature DCs), white circles represents values treated with IFN-γ, black triangles correspond to cells treated with RBL alone, white triangles correspond to cells treated with RBL+IFN-γ, and black squares correspond to cells treated with poly I:C and anti CD40.

Figure 5:
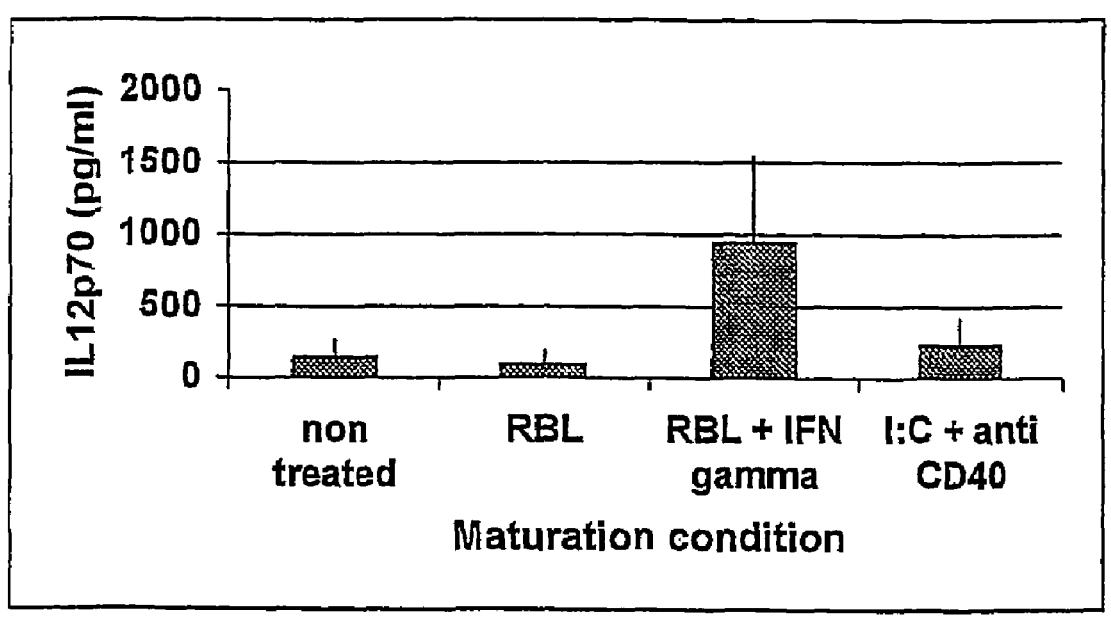

FIG. 5: IL12 secretion of mature DCs

Culture supernatants, after 40 hours of cells culture at $2.10^6$ DCs/ml, were assayed by commercial ELISA kits for IL-12 p70 cytokine secretion.

The X axis indicates the different maturation conditions used, as well as the control (non treated cells), the Y axis represents the quantity of IL12p70, in pg/ml in the culture supernatant.

Figure 6:
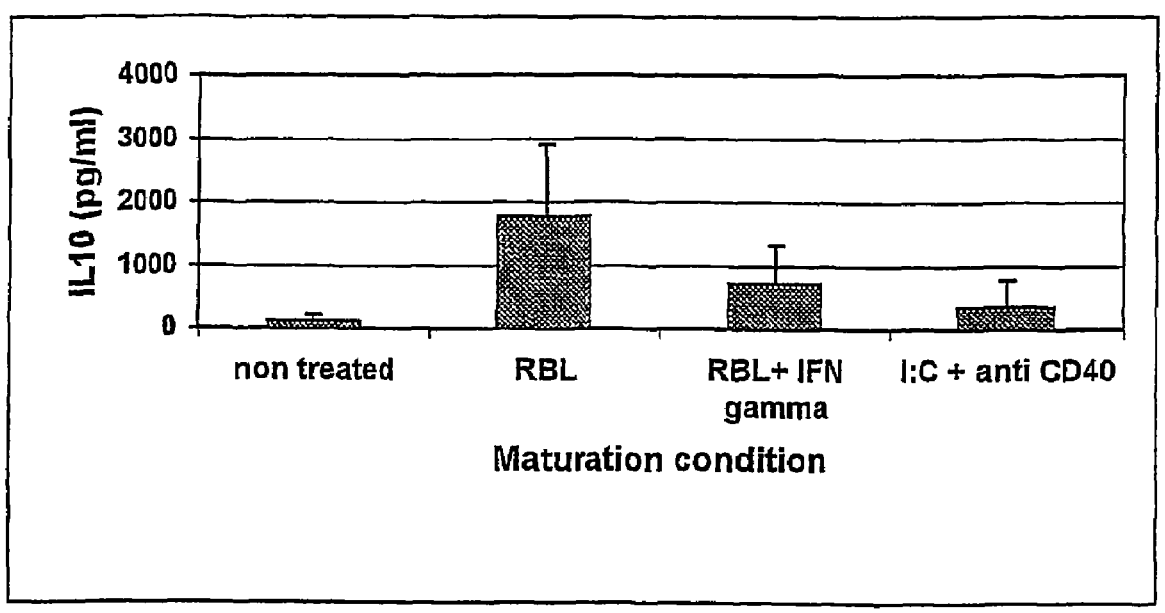

FIG. 6: IL10 secretion of mature DCs

Culture supernatants, after 40 hours of cells culture at $2.10^6$ DCs/ml, were assayed by commercial ELISA kits for EL-10 cytokine secretion.

The X axis indicates the different maturation conditions used, as well as the control (non treated cells), the Y axis represents the quantity of IL10, in pg/ml in the culture supernatant.

EXAMPLES

Example 1

Ribomunyl® Dose Response for Dendritic Cells Maturation

Dendritic Cells

Immature dendritic cells (DCs) were prepared by culture of peripheral blood monocytes and elutriated, according to the patent application WO 97/44441 and to Boyer et al. ("Generation of phagocytic MAK and MAC-DC for therapeutic use: Characterization and in vitro functional properties" Exp. Hematol., 1999, 27, 751-761). DCs were differentiated in AIMV medium supplemented with 500 U/ml GM-CSF (Leucomax, Novartis Pharma) and 50 ng/ml IL13 (Sanofi Synthelabo) (=complete AIMV medium), and elutriated after 7 days of culture. $2.10^7$ DCs/ml were then suspended in human albumin 4% and 10% dimethylsulfoxide (DMSO) and frozen in liquid nitrogen.

Maturation

The day before maturation, DCs were thawed and left overnight in complete AIMV medium containing 500 U/ml GM-CSF and 50 ng/ml IL13. Ribomunyl (RBL) (Inava laboratory, Pierre Fabre) was purchased in a pharmacy. Each vial of lyophilised RBL contains 0.010 mg of ribosomal fractions and 0.015 mg of membrane fractions. RBL is resuspended in AIMV medium (0.1 mg/ml of active fractions) extemporarily. $2.10^6$ DCs/ml were then incubated for 40 hours in the presence of doses of 0.001-0.01-0.1-1-and 10 µg/ml of Ribomunyl.

Cell Morphology

Morphology of dendritic cells obtained by blood monocytes differentiation and further treatment with Ribomunyl plus IFN-γ shows the apparition of dendrites, which are characteristics of mature DCs, those dendrites are not visible when immature DCs are observed (data not shown).

Phenotypic Analysis

To follow maturation, DCs were analysed for their expression of CD83, CD86 and HLA ABC markers. DCs were suspended in phosphate buffer saline (PBS) supplemented with foetal calf serum serum 1%, at $4.10^6$ cells/ml. 100 µl of cell suspension ($4.10^5$ cells in each tube) were incubated on ice in the dark for 30 min with fluorochrome conjugated monoclonal antibody: 10 µl of PE-conjugated mAb anti-CD83, 10 µl of PE-conjugated mAb anti-CD86 or 10 µl of FITC-conjugated anti-HLA ABC (Immunotech, Marseille, France). Cells were then washed again in PBS, centrifuged at 1400 rpm for 5 min at 20° C. and resuspended in PBS containing TO-PRO 3 at 3 nM, to exclude death cells from analysis.

Flow cytometry analysis was performed with a Becton Dickinson cytometer with a CellQuest software.

Figure 1:
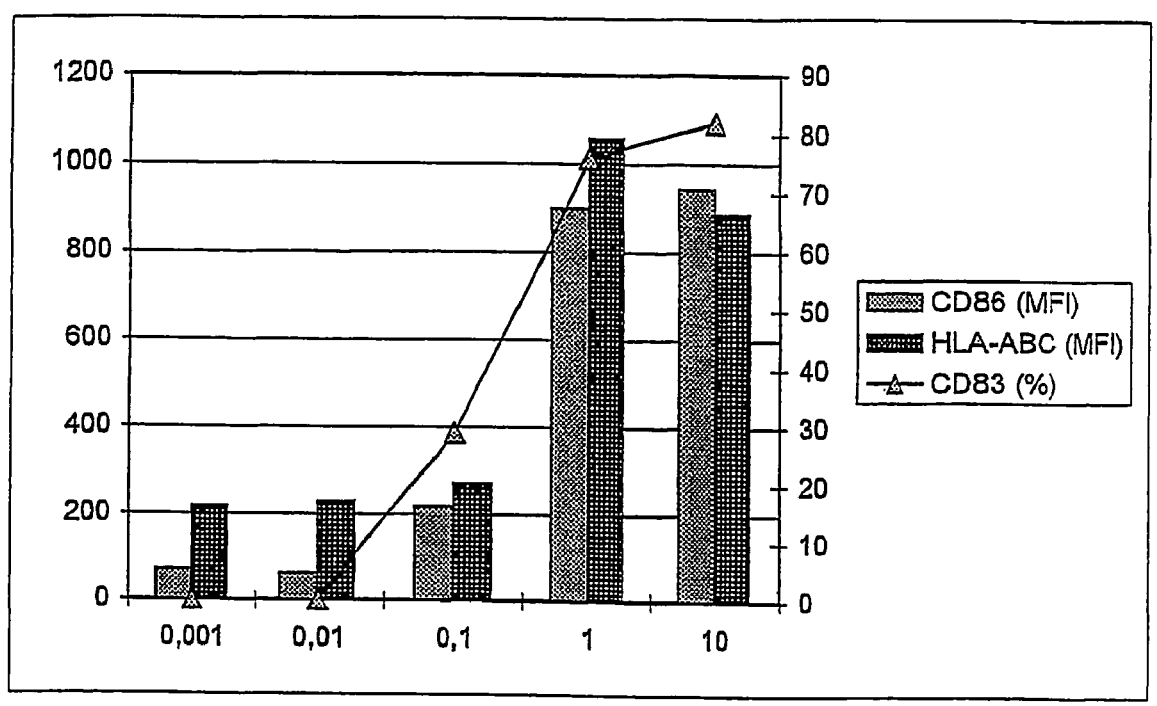
FIG. 1: Ribomunyl® dose response for dendritic cells maturation.

Results:

Results are presented on FIG. 1. Expression of CD86 and HLA-ABC markers is indicated as Mean Fluorescence Intensity arbitrary units (left Y axis) and expression of CD83 marker is indicated as a percentage of cells expressing the marker (right Y axis).

A range between 1 ng/ml and 10 µg/ml of Ribomunyl® is tested to evaluate the optimal concentration of RBL able to induce DCs maturation after 40 hours of culture with the lowest possible toxicity.

Between 1 ng/ml and 0,1 µg/ml, no maturation is obtained based on CD14, CD83, HLA-ABC and CD86 expression. Above 1 µg/ml, apparition of CD83 expression, up-regulation of CD86 and HLA ABC are seen. The cell mortality does not increase regardless of the RBL concentration used (not shown). A RBL dose of 1 µg/ml for 40 hours of maturation is therefore chosen for further studies.

Example 2

Analysis of DCs Prepared According Different Conditions Morphology of the Cells, Recovery, Mortality and Capacity to Induce T Cell Proliferation.

Cells

Immature dendritic cells were prepared as described in example 1.

$2.10^6$ DCs were incubated in complete AIMV medium for 40 hours in the presence of standard maturation reagents anti-CD40 (3 µg/ml) and poly(I:C) (100 µg/ml), in the presence of the clinical grade reagent Ribomunyl® (RBL, 1 µg/ml), or in the presence of RBL(1 µg/ml) and IFNγ (Imukin, 1000 U/ml). Culture was done in 24 well plates with $2\times10^6$ DCs/ml.

Cell Recovery and Mortality

Cell recovery after culture was estimated by counting living cells on Malassez slide. Viability of the cells is assessed by Trypan blue exclusion. Cell viability was also measured by FACS using TOPRO-3.

Phenotypic Analysis

DCs phenotype was determined by double staining flow cytometry analysis using the same markers CD83, CD86 and HLA ABC and using the same conditions than example 1, plus CD14 marker (10 µl of FITC-conjugated mAb anti-CD14, Becton Dickinson).

Allogeneic Mixed Lymphocyte Reaction (MLR)

Variable numbers of DCs (non treated, clinical grade reagent treated, or poly I:C+anti-CD40 treated) were incubated for 5 days with a fixed number of allogeneic T lymphocytes. Cell proliferation was quantified by [$^3$H] thymidine uptake of cells incubated with 1 µCi of [methyl-3H] thymidine during the last 18 hours of culture.

Results:

Cell Recovery and Mortality

The number of DCs harvested after RBL treatment during 40 hours is 1,5 fold lower than non treated DCs (FIG. 2). Cell mortality is expressed as a percentage of recovered cells.

The cell recovery after the treatment with RBL or with RBL+γIFN was inferior to that of non treated cells, the addition of IFNγ does not significantly modify the cell recovery, which remains superior to cell recovery after poly I:C plus anti CD40 treatment.

Phenotypic Analysis

DCs phenotype (FIG. 3) shows an increase of CD83 marker on the cell surface after RBL and after RBL+IFN-γ treatment. After RBL treatment, the bimodal pattern of CD83 expression shows the presence of two populations of cells, differing by their CD83 expression levels. The CD83 level of expression on RBL+IFN-γ treated cells is comparable to that of poly I:C+anti CD40 treated cells, indicative of mature cells.

Allogeneic Mixed Lymphocyte Reaction (MLR)

FIG. 4 shows that in mixed lymphocyte reaction, RBL treated DCs were 5 fold more potent stimulators than untreated or γIFN alone treated DCs. This stimulation is similar to that obtained with DCs treated with poly I:C plus anti CD40.

The addition of IFN-γ to RBL did not significantly increase the DCs capacity to induce allogeneic T cell proliferation.

Example 3

Cytokine Secretion of Dendritic Cells Matured upon Different Conditions

Cells

Immature dendritic cells were prepared as described in example 1. $2.10^6$ DCs were matured in the same conditions as the previous example.

Cytokine Detection

Culture supernatants, after 40 hours of cells culture at $2.10^6$ DCs/ml, were assayed by ELISA for IL-12 p70 and IL-10 cytokine secretion by commercial ELISA.

Cytokine production was measured in the supernatants of DCs culture using matched antibodies specific for IL12p70 (MAB611, BAF219) and for IL10 MAB217, BAF217). The assays were performed according to the manufacturer's instructions (R & D systems).

Results

RBL treatment induces production of small amounts of IL12p70. Addition of IFN-γ and RBL to DCs induced a 10 fold increase in the IL12p70 cell secretion. This value is 4 fold higher than the one obtained with poly I:C plus anti-CD40 treatment (FIG. 5).

RBL induced secretion of large amount of IL10. Addition of IFN-γ and RBL to DCs significantly decreases the level of IL10 secreted by the cells, when compared to IL10 secretion by RBL treated cells. High levels of IL12p70 are detected in supernatants of RBL plus IFN-γ treated DCs. The high level of IL10 produced by RBL treated DCs treatment significantly decreases upon IFN-γ addition (FIG. 6).

The invention claimed is:

1. A method for the preparation of mature dendritic cells from immature dendritic cells, comprising treating said immature dendritic cells with a maturation agent comprising a bacterial mixture of ribosomal fractions or ribosomal and membrane fractions to obtain mature dendritic cells.

2. The method according to claim 1, wherein the maturation agent comprises interferon-γ and a bacterial mixture of ribosomal fractions or ribosomal and membrane fractions.

3. A process for the preparation of mature dendritic cells from immature dendritic cells, said process comprising the step of contacting in a culture medium immature dendritic cells with a maturation agent comprising a bacterial mixture of ribosomal fractions or ribosomal and membrane fractions to obtain mature dendritic cells.

4. The process for the preparation of mature dendritic cells according to claim 3, wherein the maturation agent comprises interferon-γ and a bacterial mixture of ribosomal fractions or ribosomal and membrane fractions.

5. The process for the preparation of mature dendritic cells according to claim 3, wherein ribosomal fractions or ribosomal and membrane fractions are used at a dose of about 0.01 to about 100 μg/ml.

6. The process according to claim 5, wherein ribosomal fractions or ribosomal and membrane fractions are used at a dose of about 0.1 to about 10 μg/ml within the maturation medium.

7. The process according to claim 5, wherein ribosomal fractions or ribosomal and membrane fractions are used at a dose of about 10 μg/ml within the maturation medium.

8. The process for the preparation of mature dendritic cells according to claim 5, said maturation agent comprising interferon-γ is at a dose of about 10 to 10000 UI/ml within the maturation medium.

9. The process for the preparation of mature dendritic cells according to claim 8, said maturation agent comprising interferony is at a dose of about 100 to about 1000 UI/ml within the maturation medium.

10. The process for the preparation of mature dendritic cells according to claim 8, said maturation agent comprising interferon-γ is at a dose of about 1000 UI/ml within the maturation medium.

11. A method for the preparation of mature dendritic cells from immature dendritic cells, comprising treating said immature dendritic cells with a maturation agent comprising a bacterial mixture of ribosomal fractions or ribosomal and membrane fractions, and wherein the ribosomal fractions are from bacterial strains selected from the group consisting of *Klebsiella pneumoniae, Streptococcus pneumoniae, Streptococcus* pyogenes group A and *Haemophilus influenzae* to obtain mature dendritic cells.

12. The method according to claim 11, wherein the maturation agent comprises interferon-γ and a bacterial mixture of ribosomal fractions or ribosomal and membrane fractions.

13. The process for the preparation of mature dendritic cells according to claim 11, wherein the maturation agent comprises interferon-γ and a bacterial mixture of ribosomal fractions or ribosomal and membrane fractions.

14. The process for the preparation of mature dendritic cells according to claim 11, wherein the membrane fractions are from *Klebsiella pneumoniae*.

15. The process for the preparation of mature dendritic cells according to claim 11, wherein ribosomal fractions or ribosomal and membrane fractions are used at a dose of about 0.01 to about 100 μg/ml.

16. The process according to claim 15, wherein ribosomal fractions or ribosomal and membrane fractions are used at a dose of about 0.1 to about 10 μg/ml within the maturation medium.

17. The process according to claim 15, wherein ribosomal fractions or ribosomal and membrane fractions are used at a dose of about 10 μg/ml within the maturation medium.

18. The process for the preparation of mature dendritic cells according to claim 11, said maturation agent comprising interferon-γ is at a dose of about 10 to 10000 UI/ml within the maturation medium.

19. The process for the preparation of mature dendritic cells according to claim 18, said maturation agent comprising interferon-γ is at a dose of about 100 to about 1000 UI/ml within the maturation medium.

20. The process for the preparation of mature dendritic cells according to claim 18, said maturation agent comprising interferon-γ is at a dose of about 1000 UI/ml within the maturation medium.

* * * * *